United States Patent [19]

Genyk et al.

[11] Patent Number: 4,471,897
[45] Date of Patent: Sep. 18, 1984

[54] SURGICAL INSTRUMENT FOR APPLICATION OF STAPLES

[76] Inventors: Stepan N. Genyk, ulitsa Juzhny bulvar, 33, kv. 36; Vasily M. Krysa, ulitsa Makarenko, 1, kv. 1, both of Ivano-Frankovsk, U.S.S.R.

[21] Appl. No.: 368,770

[22] Filed: Apr. 15, 1982

[51] Int. Cl.³ .................... B25C 1/00; A61B 17/04
[52] U.S. Cl. .................. 227/19; 128/334 R; 128/335; 227/83; 227/87; 227/88; 227/89; 227/DIG. 1
[58] Field of Search ............. 128/334 R, 334 C, 335, 128/337; 227/DIG. 1, 8, 19, 83, 84, 85, 86, 87, 88, 89

[56] References Cited

U.S. PATENT DOCUMENTS

| | | | |
|---|---|---|---|
| 2,079,673 | 5/1937 | Allen | 227/89 X |
| 2,459,313 | 1/1949 | Franz | 227/89 X |
| 2,960,695 | 11/1960 | Hausknecht | 227/83 |
| 3,858,783 | 1/1975 | Kapitanov et al. | 227/19 X |
| 4,364,507 | 12/1982 | Savino | 227/83 |

FOREIGN PATENT DOCUMENTS 189982 12/1966 U.S.S.R. .
419001 3/1974 U.S.S.R. .

Primary Examiner—Paul A. Bell
Attorney, Agent, or Firm—Fleit, Jacobson, Cohn & Price

[57] ABSTRACT

A surgical instrument comprises an elongated body having a working zone at a distal end thereof. Kinematically connected between themselves and disposed within the body are: a mechanism for feeding wire into the working zone of the body, a mechanism for forming U-shaped staples from the wire, and a mechanism for reshaping U-shaped staples into rectangular ones, provided with a driver and anvils. The driver is connected with a reciprocating drive along the longitudinal axis of the body and is provided with a working portion in the form of two V-shaped projections. The anvil is disposed in the working zone of the body perpendicularly to its longitudinal axis in a plane of motion of the driver so that it can be moved out of this plane. The length of the anvil is less than the transverse side of the U-shaped staple.

6 Claims, 10 Drawing Figures

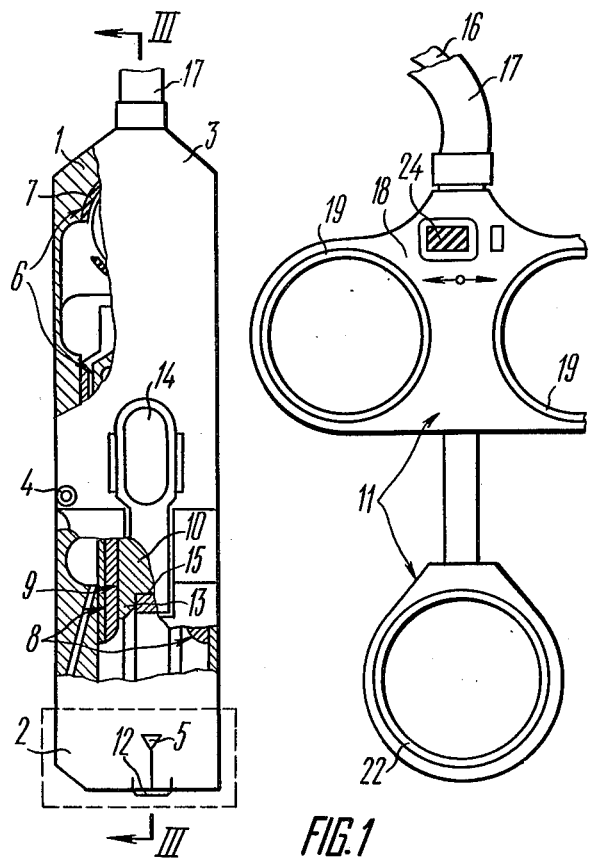
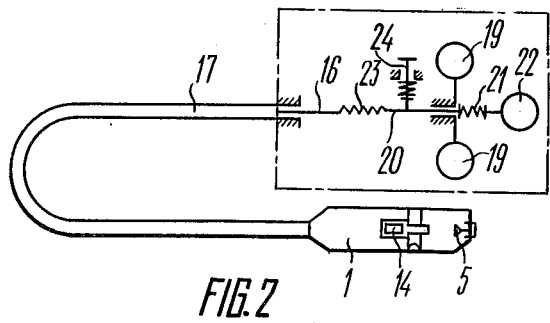

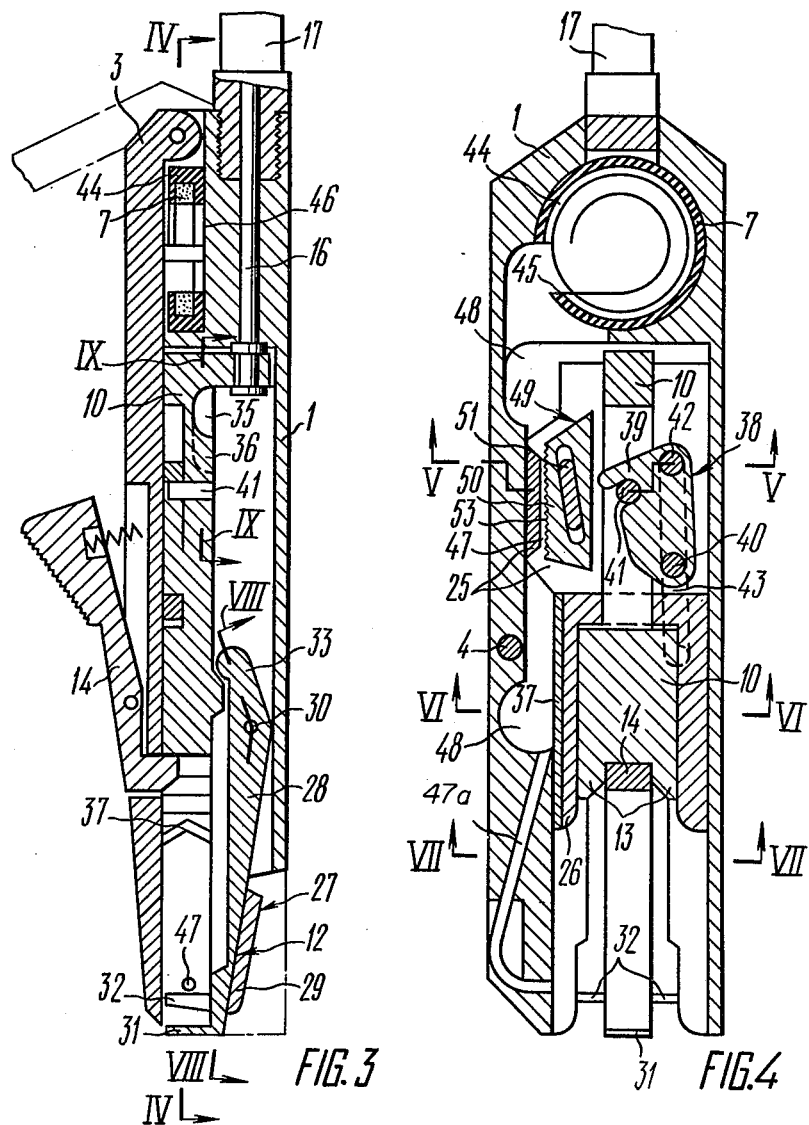

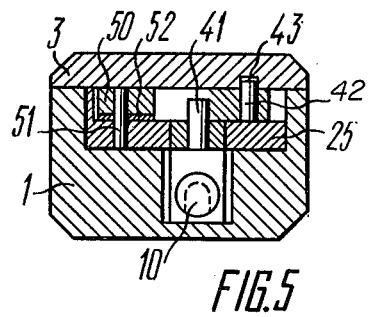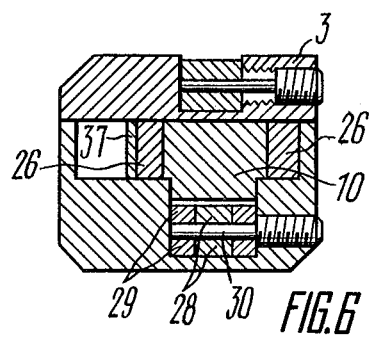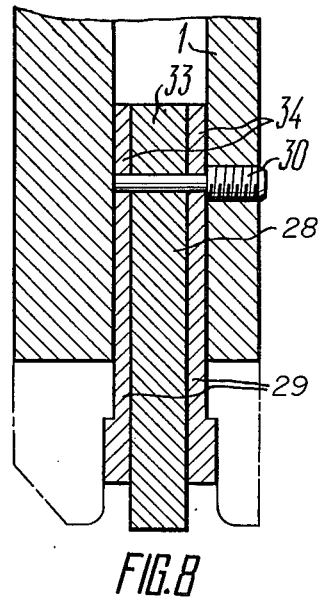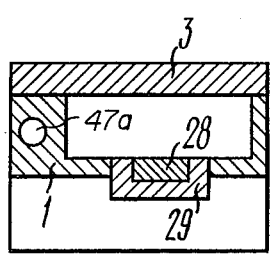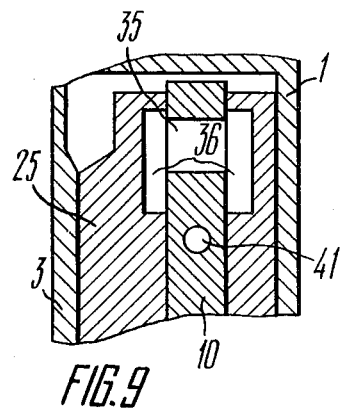

SURGICAL INSTRUMENT FOR APPLICATION OF STAPLES

FIELD OF THE INVENTION

The present invention relates to medical equipment, and particularly to medical instruments for application of staples.

The invention may prove most advantageous in surgical intervention when applying sutures to various organs and soft tissues of an organism.

At present in different countries staples are intensively used in surgical operations instead of ligature filaments for application of sutures. This fact was promoted by such factors as a higher reliability of staple sutures, a decrease in the possibility of occurrence of inflammatory process along the suture line, the prime consideration consisting in simplicity and high rate of application of the staple suture.

There are many various instruments for application of staples, which, according to the principle of the action thereof, can be divided into two types.

When the first type of instruments is used, a bearing female die with pits is brought under the tissue to be sutured to bend U-shaped staples and is used in application of staples to blood vessels, gastrointestinal tract organs, bronchi, lungs and other organs and soft tissues under which the bearing female die can be brought to bend the staples.

When the second type of instruments is used, to suture tissues, the bearing female die is not brought thereunder, as, for instance, in suturing skin, hypodermic fat, muscles, fasciae, aponeurousises, as well as in application of staples to eye tissues.

When making such instruments for application of staples, designers tried to reduce dimensions and weight thereof and at the same time to decrease unproductive time expenditures required for replacement or recharging of the surgical instrument. Analysis of the prior art proves that up to now this problem has not been adequately solved.

Of the instruments of the second type there is known an apparatus for suturing akin by U-shaped metal staples as described in USSR Inventor's Certificate No. 189,982, published July 16, 1966. Said apparatus comprises an elongated body with a grip, said body having a working zone at the distal end thereof. Within the body there are arranged an accessory magazine yoke for U-shaped staples, a spring-loaded feeder with a drive for moving thereof along the longitudinal exis of the body, and a stationary anvil for fixing the medium portion of the staple, which anvil is disposed in parallel with the axis of the body and kinematically connected with the driver. Such shape of the staple does not ensure holding the tissues being sutured in a close relation, because the staple can easily fall out of the sutured tissues.

This disadvantage is overcome in a surgical instrument which makes it possible to form rectangular staples in the course of application which reliably hold sutured tissues as described in USSR Inventor's Certificate No. 419,001, published Mar. 5, 1974. This instrument comprises an elongated body having a working zone at a distal end thereof. Within the body there are arranged an accessory yoke for U-shaped staples, kinematically connected with a mechanism for feeding the staples into the working zone of the body, and a mechanism for reshaping the U-shaped staples into rectangular ones in the course of application of the staples. The reshaping mechanism comprises a driver and an anvil. The driver is connected with a reciprocating drive for moving along the longitudinal axis of the body and has a working portion in the form of two V-shaped projections. The anvil is arranged in a plane of motion of the driver so that the anvil having a length less than the transverse side of a U-shaped staple can be moved out of this plane.

An obvious advantage of the above-described surgical instrument consists in that it allows quick application of one or several quality sutures to organs and tissues without replacement or recharging of the instrument. However, in practical use of this instrument there occur a number of difficulties which deteriorate the operation characteristics of the instrument and lead to undesirable postoperative consequences.

This is due to the fact that at present a wide range of staples of various sizes is produced at factories, whereas charging of the staple yoke as a rule is to be carried out in a hospital before operation. Such being the case, charging of the staple yoke with tiny staples whose size is not more than 1.5 to 2 mm requires certain habits, and is labor and time consuming (it takes up to 1 hour). Besides, in view of a wide range of staples of various standard sizes the staple yoke is sometimes charged with staples of other sizes than required, or with deformed staples.

In one case it may lead to seizure of the staples in the yoke or at the outlet therefrom, which makes it necessary to interrupt the operation for recharging said yoke.

In another case (when a wrongly charged yoke was of a size less than necessary) a wrongly charged staple (or staples) in operation of the instrument and suturing of tissues may result in not sufficiently strong suture and connection of the tissues being treated, which leads to discontinuity of the suture in postoperative period, to bleeding and even to fatal termination. Similar negative consequenes are liable to occur even if the yoke was charged in a proper way, when at least one staple was damaged or deformed while being installed into the yoke. It is to be noted that such damage is possible, since the diameter of the wire from which staples are made in some cases is not more than 0.1 mm.

In addition, it is to be noted that the yoke disposed close to the working zone of the body of the instrument substantially increases the sizes of the instrument in this zone, which reduces the possibilities of manipulation with the instrument in the operation zone.

SUMMARY OF THE INVENTION

A principal object of the present invention is to provide a surgical instrument for application of staples, which makes it possible to produce staples from wire in the course of making a suture.

Another object of the invention is to reduce the time required for preparation of the instrument for operation.

Another object of the invention is to provide an instrument which makes it possible to quickly make high-quality sutures and is of a comparatively small size.

Another object of the invention is to upgrade the quality of the suture.

Another object of the invention is to provide an instrument which is more convenient in operation.

Another object of the invention is to provide an instrument which is more reliable in operation.

Another object of the present invention is to preclude the possibility of seizure of the instrument in the course of making a suture.

These and other objects of the present invention are attained by that there is provided an instrument for application of staples, comprising an elongated body having a working zone at the distal end thereof, a mechanism for reshaping U-shaped staples into rectangular ones, mounted within the body and having a driver connected with a reciprocating drive to be reciprocated along the longitudinal axis of the body and provided with a working portion in the form of two V-shaped projections and with an anvil disposed in the working zone of the body perpendicularly to its longitudinal axis in a plane of motion of the driver so that the anvil having a length less than the transverse side of the U-shaped staple can be moved out of this plane, wherein, according to the invention, the body incorporates a mechanism for feeding a wire stock into the working zone of the body and a mechanism for forming U-shaped staples from the wire stock, kinematically connected between themselves and with the mechanism for reshaping U-shaped staples into rectangular ones.

Such a surgical instrument allows the U-shaped staples to be formed from the wire in the course of making a suture. This makes it possible to preclude the operation of charging the instrument and, consequently, mistakes mentioned hereinbefore.

It is also to be noted that the preparation of the staples in the course of making a suture precludes the possibility of any mechanical damage thereof, as it occurred in charging the yoke of conventional instruments with wire.

The elimination of the yoke has allowed the sizes of the instrument (particularly, the working zone of the body) to be reduced without affecting the productivity thereof. This contributed to a higher reliability of the suture and reduced traumatism in the sections of the operation field which are difficult to approach.

An important advantage of the instrument of the invention consists in that the preparation thereof for operation is limited only to insertion of the end of the wire into a passage for feeding this wire into the working zone of the body (instead of charging the yoke with the wire). Such being the case, the time required to prepare the instrument for operation does not depend on the size of the staples. The period of preparation of the instrument of the invention for operation is less by 10 to 15 times as compared with the conventional instruments for application of staples.

Simple in construction and reliable in operation is a modification of the instrument of the invention, wherein the mechanism for forming U-shaped staples is made in the form of a frame mounted within the body for reciprocating motion along the longitudinal axis thereof and having a U-shaped working portion incorporating the driver installed for reciprocating motion therein and detachably connected with said frame, and of an anvil disposed in the working zone of the body perpendicularly to the longitudinal axis thereof in a plane of motion of the frame so that the anvil can be moved out of this plane, the working portion of the frame having a width equal to the length of an unrolled section of the wire forming a U-shaped staple and being displaced with respect to the working portion of the driver towards the working zone of the body by the length of the leg of a U-shaped staple, and the anvil of the mechanism for forming U-shaped staples having a length less than the transverse side of the U-shaped staple and being displaced with respect to the anvil of the mechanism for reshaping U-shaped staples into rectangular ones in the direction opposite that of the working zone of the body by the length of a leg of a U-shaped staple.

It is advisable that on one of the lateral walls of the working portion of the frame there be secured a cutter for cutting off measured sections of the wire, the cutter being arranged at an angle to the axis of the wire.

To ensure synchronous and reliable operation of the instrument, it is advisable that the driver and the frame be detachably connected by means of a disconnector made in the form of a L-shaped clip pivoted to the frame and intended to interact with a projection of the driver, the clip having a projection introduced into a L-shaped slot of the housing.

The most compact and simple in construction is a modification of the instrument of the invention, wherein the mechanism for feeding the wire is made in the form of a spool with the wire stock, mounted in a socket provided in the wall of the body and communicating with a passage to feed the wire into the working zone of the body and of a wire gripping and delivering assembly mounted on the frame of the mechanism for forming U-shaped staples.

It is advisable that in this modification of the instrument the wire gripping and delivering assembly be made in the form of a plate movably mounted on an inclined projection secured to the frame and having a working surface interacting in the working position with the lateral well of the frame and forming therewith a portion of the passage to feed the wire into the working zone of the body.

BRIEF DESCRIPTION OF THE DRAWINGS

The invention will now be explained in greater detail with reference to embodiments thereof which are represented in the accompanying drawings, wherein:

FIG. 1 diagrammatically shows a general view of the surgical instrument for application of staples according to the invention, with partial sections;

FIG. 2 shows a kinematic diagram of the drive for reciprocating motion of the driver;

FIG. 3 shows a cross-section along line III—III in FIG. 1 of the drawings;

FIG. 4 shows a cross-section along line IV—IV in FIG. 3 of the drawings;

FIG. 5 shows a cross-section along line V—V in FIG. 4 of the drawings;

FIG. 6 shows a cross-section along line VI—VI in FIG. 4 of the drawings;

FIG. 7 shows a cross-section along line VII—VII in FIG. 4 of the drawings;

FIG. 8 shows a cross-section along line VIII—VIII in FIG. 3 of the drawings;

FIG. 9 shows a cross-section along line IX—IX in FIG. 3 of the drawings;

DETAILED DESCRIPTION OF THE PREFERRED EMBODIMENTS

Figure 10:
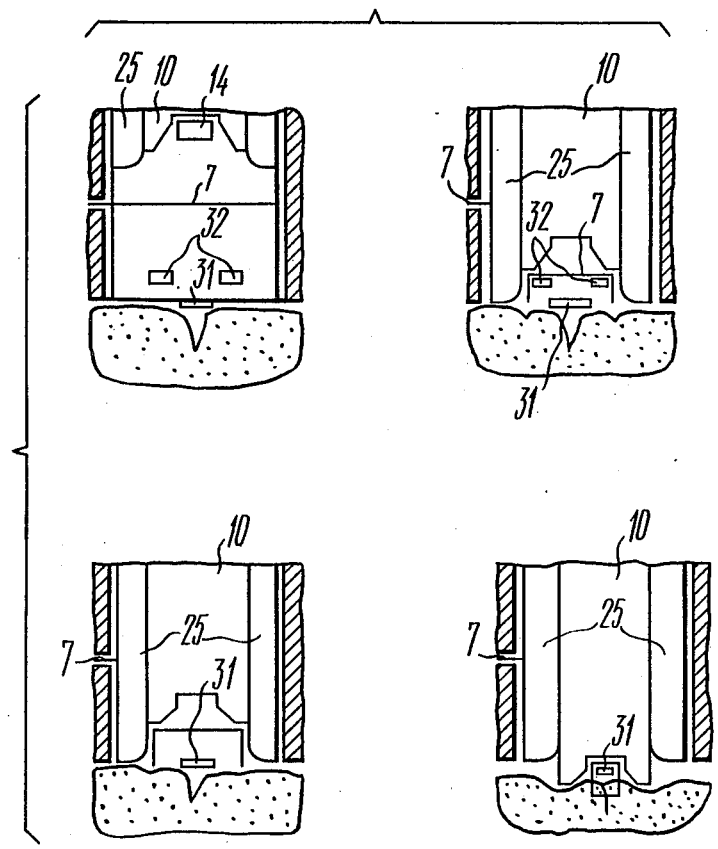
FIG. 10 shows a sequence diagram illustrating interaction of elements of the surgical instrument while performing the operation of making a suture.

The proposed surgical instrument for application of staples comprises an elongated body 1 (FIG. 1) having a working zone 2 at the distal end thereof. The elongated body 1 is a box-like structure having a complicated internal surface. The body 1 is provided with a cover 3 rotatively mounted on the body 1 and provided with a fixator 4 to fix the cover 3 in the closed position. The fixator 4 is installed in the wall of the body 1. On the distal end of the cover 3 of the body 1 there is provided a guide 5 for orientation of a staple with respect to a suture.

Within the inner space of the housing 1, formed by the walls of the body 1 and the cover 3 there are mounted all the main mechanisms of the instrument: a mechanism 6 for feeding a wire 7 into the working zone 2 of the body 1, a mechanism 8 for forming U-shaped staples from the wire 7, kinematically connected with the mechanism 6 for feeding the wire 7 and with a mechanism 8 for forming U-shaped staples.

A mechanism 9 for reshaping U-shaping staples into rectangular ones comprises a driver 10 connected with a reciprocating drive 11 serving for reciprocating said driver 10 along the axis of the body 1, and an anvil 12 arranged in the working zone 2 of the body 1 perpendicularly to the longitudinal axis thereof in a plane on motion of the driver 10 so that the anvil 12 can be moved out of this plane. The driver 10 has a working portion in the form of two V-shaped projections 13, each of the projections 13 having a groove for U-shaped staples.

The length of the anvil is less than the transverse side of the U-shaped staple. The distance between the V-shaped projections 13 of the driver 10 is equal to the length of the anvil 12 plus double value of the diameter of the wire 7 and plus a small clearance provided to prevent seizure of the U-shaped staples.

On the cover 3 of the body 1 there is pivotally mounted a spring-loaded latch 14 introduced into a slot 15 formed by the projections 13 of the driver 10 and serving for locking the latter.

It will be understood that the drive 11 for reciprocating the driver 10 along the longitudinal axis of the body 1 may be variously constructed. It may be mechanical, pneumatic, or hydraulic. In addition, in the proposed driver the surgical instrument the drive 11 may be either incorporated in one block together with the body 1, or autonomous. From the point of view of human engineering it is advisable that an autonomous drive 11 be used, because the provision of the instrument in a common assembly will not ensure exact orientation of the staple with respect to the line of the suture, which impairs the quality of the suture. When the autonomous drive 11 is used, the orientation of the guide 5 of the instrument with respect to the tissues being sutured is carried out by one hand (or only the surgeon who operates), and the drive 11 is switched on by the outer hand (or the assistant), which is of particular importance when small sutures are made or when manipulations in deep wounds are to be done.

In this case there was used an autonomous mechanical drive 11 which is most simple and reliable in operation. The drive 11 (FIGS. 1 and 2) is kinematically connected with the driver 10 through a cable release 16 which ensures transmission of forces. The cable release has a sheath 17. The connection between the pusher 10 and the cable release 16 is movable, which provides for a mutual free travel of the pusher 10 and the cable release 16. The sheath 17 of the cable release 16 is secured to a body 18 of the drive 11, wherein two circular gandles 19 are provided. Within the body 18 there is a reciprocatingly mounted pusher 22 whose one end is connected through a spring 23 with the cable release 16.

The pusher 22 is provided with a spring-loaded latch 24 for fixation thereof when the spring 21 is compressed.

The mechanism 8 for forming U-shaped staples from the wire 7 may be variously constructed. FIGS. 3–9 show the mechanism comprising a frame 25 mounted within the body 1 for reciprocating motion along the longitudinal axis thereof. The frame 25 has U-shaped working portion 26 encompassing the working portion of the driver 10 of the mechanism 9. The driver 10 is mounted in the working portion 26 of the frame 25 for reciprocating motion with respect to the latter. The working portion 26 of the frame 25 has a width equal to the length of the unrolled section of the wire 7 forming a U-shaped staple and is displaced with respect to the working portion of the driver 10 towards the working zone 2 of the body 1 by the length of a leg of the U-shaped staple.

The mechanism 8 also comprises an anvil 27 disposed in the working zone 2 of the body 1 perpendicularly to the longitudinal axis thereof in a plane of motion of the frame 25 so that the anvil 27 can be moved out of this plane. The anvil 27 has a length less than the transverse side of the U-shaped staple and is displaced with respect to the anvil 12 of the mechanism 9 for reshaping U-shaped staples into rectangular ones in the direction opposite to that of the working zone 2 of the body 1 by the length of a leg of the U-shaped staple.

Both the anvil 12 of the mechanism 9 and the anvil 27 of the mechanism 8 are made in the form of two-armed L-shaped levers, respectively 28 and 29, mounted on an axle 30 secured to the body 1 as best seen in FIGS. 3 and 8 of the drawings.

On one arm of each two-arm lever 28 and 29 there are provided support surfaces, respectively 31 and 32, disposed perpendicularly to the longitudinal axis of the body, and on the other arm there are provided projections, respectively 33 and 34 to be received, if necessary, in the corresponding cut-outs, respectively 35 and 36. The cut out 35 is made in the driver 10, and the cut-out 36, in the frame 25. The configuration of the cut-outs 35 and 36 is selected in accordance with the motion of the mechanisms 8 and 9. Such being the case, the support surfaces 31 and 32 of the levers 28 and 29 as well as the cut-outs 35 and 36 are disposed at a distance equal to the length of a leg of the U-shaped staple.

On one of the lateral walls of the working portion 26 of the frame 25 there is attached a cutter 37 (FIG. 4) to cut off measured sections of the wire 7. The cutter 37 is accessory for convenience purposes and for replacement if necessary and is installed at an angle to the axis of the wire 7 being cut off.

The mechanisms 8 and 9 are kinematically connected between themselves by means of a disconnector 38 (FIGS. 4 and 5). The disconnector 38 is made in the form of a an L-shaped clip pivotally secured to the frame 25 by means of an axis 40. The L-shaped clip 39 interacts with the projection 41 of the driver 10 and is provided with a projection 42 introduced into the L-shaped slot 43 made in the cover 3 of the body 1.

The mechanism 6 for feeding the wire 7 into the working zone 2 of the body 1 can be variously constructed. The most compact and reliable in operation is a modification of the instrument, shown in FIGS. 3 and 4 of the drawings. The mechanism 6 for feeding the wire 7 comprises a spool 44 with the wire 7. The spool 44 is made in the form of a ring provided with an internal passage and a slot 45 serving for visual observation of the placement of the wire 7 and for orientation of the spool 44 at the time of the installation thereof. The spool 44 is installed in a socket 46 made in the wall of the body 1. The socket 46 communicates with the working zone 2 of the body 1 by means of a passage or channel 47 for feeding the wire 7 into said working zone 2. The channel 47 is of a predetermined configuration. For convenience of placement of the wire 7 into the passage 47, the wall of the body 1 is provided with cavities 48 for jaws of the forceps.

The mechanism 6 also comprises a wire gripping and delivering assembly 49 mounted on the frame 25 and kinematically connecting the mechanism 6 and the mechanism 8. Said wire gripping and delivering assembly 49 for delivering the wire into the working zone 2 of the body 1 comprises a plate 50 (FIGS. 4 and 5) movably disposed on an inclined projection 51 secured to the frame 25 and spring-loaded by a leaf spring 52 installed on the same projection 51 to the cover 3 of the body 1. The plate 50 is provided with a knurled surface 53 interacting in the working position with the lateral wall of said frame 25 and forming therewith a portion of the passage 47 for feeding the wire 7 into the working zone 2 of the body 1.

FIG. 10 shows a sequence diagram representing the stages of bending of the rectangular staples and introduction thereof into the tissue being sutured. This Figure illustrates an interaction between the elements of the surgical instrument in the course of making a suture.

The surgical instrument operates in the following manner.

Prior to operation the instrument should be charged with the wire 7 and sterilized. For this purpose, the end of the wire 7 is withdrawn from the spool 44 (FIGS. 3 and 4) with forceps, the end of the wire 7 having a length of 5-6 cm which is sufficient for placing it into the mechanism 6. Then the cover 3 of the body 1 is removed and the spool 44 is placed into the socket 46, whereupon the wire with the forceps is placed into the portion of the passage 47, formed by the working surface 53 of the plate 50 and the lateral wall of the frame 25 (FIG. 4) and then into the bent passage 47a to feed the wire 7 into the working zone of the body 1. After charging the instrument with the wire 7 the cover 3 is replaced by pressing the outer surface thereof by hand till the fixator 4 operates. Thus the instrument is prepared for operation.

To check the readiness of the instrument for operation, several staples are made on the idle run of the instrument. For this purpose, the following manipulations are resorted to: the drive is taken by left hand (FIGS. 1 and 2) in such a way that the forefinger and the middle finger pass into the ring holders 19 and the thumb into the pusher 22. The body 1 of the instrument is taken by right hand so that it is convenient to press the spring-loaded latch 14 by the thumb and the forefinger.

By pressing the pusher 22 of the drive 11 the spring 21 is cocked and upon the coincidence of the guide 5 of the cover 3 of the instrument with the section of the tissue being sutured the spring-loaded latch 14 is pressed. The mechanisms of the instrument automatically make U-shaped staples and then reshape them into rectangular ones. The ready staples are released from the support surfaces 31 and 32 of the anvils 12 and 27. Thus, even without the tissue to be sutured, it is possible to obtain ready rectangular staples, which fact is used for checking the operation of the instrument.

The mechanisms and elements of the instrument in operation interact in the following manner.

From the spring 21 of the drive 11 the effort is transmitted through the cable release 16 to the driver 10 of the mechanism 9 (FIGS. 1, 2 and 3) which starts moving towards the working zone 2 of the body 1 (FIG. 4). Since the driver 10 of the mechanism 9 is kinematically connected with the frame 25 of the mechanism 8 by means of the disconnector 38, they move together until the projection 42 of the clip 39 of the disconnector enters the inclined portion of the L-shaped slot 43 of the cover 3 of the body 1.

Simultaneously therewith, the wire 7 is fed into the working zone of the body 1. Such being the use, the frame 25 moves the inclined projection 51, due to which the plate 50 presses the wire 7 to the lateral wall of said frame 25 by its knurled working surface 53 and starts moving it towards the working zone 2. The feeding of the wire 7 into the working zone is discontinued when the frame 25 stops, and when the frame 25 moves in the opposite direction, the wire is released, since the plate 50 moves away from the lateral wall of the frame 25 and thereby a free travel of the wire 7 is provided for.

U-shaped staples are formed when the working portion 26 of the frame 25 moves towards the working zone 2 of the body up to the stop. In so doing, a measured section of the wire 7 is cut off with a cutter 37, and a U-shaped staple is formed. The staple formation starts from the moment when the ends of the U-shaped working portion 26 of the frame 25 pass by the support surfaces 32 of the anvil 27. The ends of the working portion 26 of the frame 25 press the ends of the measured section of the wire 7 and bend them around the support surfaces 32 by an angle of 90°, thereby forming a U-shaped staple (FIG. 10).

As noted before, the frame 26 moves together with the pusher 10 till the projection 42 of the clip of the disconnector enters the inclined portion of the L-shaped slot 43 of the cover 3 of the body 1. In so doing, the clip 39 moves aside and thereby, disengages the projection 41 of the driver 10 which moves farther alone, thus ensuring the formation of a rectangular staple from a U-shaped one. Such being the case, the support surface 32 of the anvil 27 of the mechanism 8 moves out of the plane of motion of the frame 25 (and, respectively, of the driver 10) due to the motion of the lever 29 at the moment when the projection 34 thereof is in the cut-out 36 provided in the driver 10.

The formation of a rectangular staple starts from the moment of pressing a U-shaped staple to the support surface 31 of the anvil 12 of the mechanism 9. With the motion of the driver 10, due to the provision of grooves in its V-shaped projections 13 the U-shaped staple is easily bent around the support surface 31 of the anvil 12 and acquires a rectangular shape (FIG. 10). Then the support surface 31 of the anvil 12 of the mechanism 9 is moved out of the plane of motion of the pusher due to the motion of the lever 28 at the moment when the projection 33 thereof is introduced into the cut-out 35 provided in the driver 10.

The surgical instrument is removed from the damaged section of the tissue, and all the parts thereof are brought to the initial position. The sutured damaged section is distributed and fills out the space under the staple. Then the instrument is pressed to the next point of the damaged section, and another staple is applied and so on till the whole damaged section is sutured.

It will be understood that described herein are only some modifications of the proposed surgical instrument for application of staples. Various other modifications and alterations are possible within the spirit and scope of the invention as defined in the claims.

What we claim is:

1. A surgical instrument for application of staples, comprising:

an elongated body having a working zone at the distal end thereof;

a mechanism mounted within said body for feeding a wire into the working zone of the body;

a mechanism mounted within said body for forming U-shaped staples from the wire and kinematically connected with the mechanism for feeding the wire, said forming mechanism including a first anvil and a driver cooperable with said first anvil;

a mechanism for reshaping U-shaped staples into rectangular staples, said reshaping mechanism mounted within said body and kinematically connected with said mechanism for feeding the wire and with said mechanism for forming U-shaped staples, said reshaping mechanism including a second anvil, said second anvil being narrower than said first anvil for forming a rectangular staple from said U-shaped staple, said rectangular staple being narrower than said U-shaped staple;

said driver provided with a working portion in the form of a pair of spaced projections cooperable with said first anvil for forming a U-shaped staple from a length of wire and two spaced, V-shaped projections for forming a rectangular staple, said driver connected with a drive enabling reciprocating motion thereof along the longitudinal axis of said body;

said first and second anvils disposed within the working zone of said body perpendicularly to the longitudinal axis thereof in a plane of motion of said driver, said first anvil having a length less than the transverse side of a U-shaped staple and movable out of said plane of motion.

2. A surgical instrument as claimed in claim 1, wherein said mechanism for forming U-shaped staples comprises:

a frame mounted within said body for reciprocation along the longitudinal axis thereof and having a U-shaped working portion wherein said driver is installed for reciprocating motion and detachably connected with said frame, the working portion of said frame having lateral walls and a width equal to the length of an unrolled section of the wire forming a U-shaped staple and is displaced with respect to the working portion of said driver towards the working zone of said body by the length of a leg of the U-shaped staple;

said first anvil disposed in the working zone of said body perpendicularly to the longitudinal axis thereof in a plane of motion of said frame so that said first anvil can be moved out of said plane, said first anvil having a length less than the transverse side of the U-shaped staple and being displaced with respect to said second anvil in a direction outside the working zone of said body the length of a leg of the U-shaped staple.

3. A surgical instrument as claimed in claim 2, wherein on one of the lateral walls of the working portion of the frame there is secured a cutter for cutting off measured sections of the wire, the cutter being arranged at an angle to the axis of the wire.

4. A surgical instrument for application of staples, comprising:

an elongated body having a working zone at the distal end thereof;

a mechanism mounted within said body for feeding a wire into the working zone of the body;

a mechanism mounted within said body for forming U-shaped staples from the wire and kinematically connected with the mechanism for feeding the wire;

a mechanism for reshaping U-shaped staples into rectangular ones, mounted within said body and kinematically connected with said mechanism for feeding the wire and with said mechanism for forming U-shaped staples;

a driver provided with a working portion in the form of two V-shaped projections and connected with a drive enabling reciprocating motion thereof along the longitudinal axis of said body;

an anvil disposed within the working zone of said body perpendicularly to the longitudinal axis thereof in the plane of motion of said driver so that the anvil has a length less than the transverse side of a U-shaped staple and can be moved out of said plane, said anvil having a length less than the transverse side of the U-shaped staple and being displaced with respect to an anvil of the mechanism of reshaping U-shaped staples into rectangular ones in the direction opposite that of the working zone of said body and of the length of a leg of the U-shaped staple;

a frame mounted within said body for reciprocating along the longitudinal axis thereof and having a U-shaped working portion wherein a driver is installed for reciprocating motion, detachably connected with said frame, the working portion of said frame having a width equal to the length of an unrolled section of the wire forming a U-shaped staple and is displaced with respect to the working portion of said driver towards the working zone of said body by the length of a leg of the U-shaped staple; and the driver and the frame are detachably connected by means of a disconnector made in the form of an L-shaped clip pivoted to the frame and intended to interact with a projection of the driver, the clip having a projection introduced into an L-shaped slot of the housing.

5. A surgical instrument as claimed in claim 1, wherein the mechanism for feeding the wire is made in the form of a spool with the wire, mounted in a socket provided in the wall of the body and communicating with a passage to feed the wire into the working zone of the body and of a wire gripping and delivering assembly mounted on the frame of the mechanism for forming U-shaped staples.

6. A surgical instrument as claimed in claim 5, wherein the wire gripping and delivering assembly is made in the form of a plate movably mounted on an inclined projection secured to the frame and having a working surface interacting in the working position with the lateral wall of the frame and forming therewith a portion of the passage to feed the wire into the working zone of the body.

* * * * *